US008905918B2

(12) United States Patent
Kato

(10) Patent No.: US 8,905,918 B2
(45) Date of Patent: Dec. 9, 2014

(54) ENDOSCOPE SYSTEM

(75) Inventor: Shuichi Kato, Tokyo (JP)

(73) Assignee: Olympus Corporation, Tokyo (JP)

( * ) Notice: Subject to any disclaimer, the term of this patent is extended or adjusted under 35 U.S.C. 154(b) by 471 days.

(21) Appl. No.: 13/250,465

(22) Filed: Sep. 30, 2011

(65) Prior Publication Data

US 2012/0083655 A1    Apr. 5, 2012

(30) Foreign Application Priority Data

Sep. 30, 2010    (JP) ................................ P2010-220157

(51) Int. Cl.
| | | |
|---|---|---|
| A61B 1/04 | (2006.01) | |
| A61B 1/06 | (2006.01) | |
| A61B 1/00 | (2006.01) | |
| H04B 17/00 | (2006.01) | |
| A61B 3/00 | (2006.01) | |

(52) U.S. Cl.
CPC ......... *A61B 1/00165* (2013.01); *A61B 1/00013* (2013.01); *A61B 1/00055* (2013.01); *A61B 3/0058* (2013.01)
USPC ............. 600/109; 600/182; 600/101; 398/17; 398/9

(58) Field of Classification Search
CPC .... A61B 1/07; A61B 1/00163; A61B 5/1455; A61B 19/5225; H04J 14/02; G02B 2006/12164
USPC ............ 600/109, 182, 476, 160, 101; 606/15, 606/16; 398/79, 48, 66, 135, 128, 140, 174, 398/176, 17, 9; 359/325, 238; 348/45, 65
See application file for complete search history.

(56) References Cited

U.S. PATENT DOCUMENTS

| | | | | |
|---|---|---|---|---|
| 4,910,590 | A  * | 3/1990 | Gillies et al. ..................... | 348/65 |
| 6,628,214 | B1 * | 9/2003 | Kawase et al. ................ | 341/100 |
| 7,440,702 | B2 * | 10/2008 | Imai .............................. | 398/141 |
| 7,444,446 | B2 * | 10/2008 | Yamaguchi et al. .......... | 710/106 |
| 7,548,675 | B2 * | 6/2009 | Tatum et al. .................. | 385/100 |
| 7,706,692 | B2 * | 4/2010 | Tatum et al. .................. | 398/139 |
| 7,729,618 | B2 * | 6/2010 | Tatum et al. .................. | 398/139 |
| 8,152,712 | B2 * | 4/2012 | Abe ............................. | 600/103 |

(Continued)

FOREIGN PATENT DOCUMENTS

| | | |
|---|---|---|
| JP | 61-121590 A | 6/1986 |
| JP | 04-329923 A | 11/1992 |

(Continued)

OTHER PUBLICATIONS

Office Action dated Mar. 4, 2014, issued in Japanese Patent Application No. 2010-220157 with English Translation (4 pages).

*Primary Examiner* — John P Leubecker
*Assistant Examiner* — Ronald D Colque
(74) *Attorney, Agent, or Firm* — Westerman, Hattori, Daniels & Adrian, LLP

(57) ABSTRACT

An image pickup portion picks up an image of a suspected substance and produces a video signal. Optical fibers transmit the video signal output from the image pickup portion. A video signal processing portion processes the video signals transmitted by the optical fibers and then outputs the processed video signals to a monitor. A trouble detection portion detects trouble in a transmission state of the optical fibers. The video signal processing portion outputs to the monitor only the video signal transmitted by the optical fiber in which the trouble detection portion has not detected trouble.

8 Claims, 6 Drawing Sheets

(56) References Cited

U.S. PATENT DOCUMENTS

| | | | |
|---|---|---|---|
| 8,233,805 B2* | 7/2012 | Tatum et al. | 398/141 |
| 8,452,181 B2* | 5/2013 | Yasuda et al. | 398/115 |
| 8,559,826 B2* | 10/2013 | Hongo et al. | 398/155 |
| 2004/0132412 A1* | 7/2004 | Plett et al. | 455/69 |
| 2004/0263941 A1* | 12/2004 | Chen et al. | 359/245 |
| 2005/0034172 A1* | 2/2005 | Nohara et al. | 725/147 |
| 2005/0046744 A1* | 3/2005 | Ohkubo et al. | 348/489 |
| 2005/0063707 A1* | 3/2005 | Imai | 398/141 |
| 2005/0089066 A1* | 4/2005 | Soga et al. | 370/498 |
| 2005/0094676 A1* | 5/2005 | Iwami et al. | 370/527 |
| 2005/0105900 A1* | 5/2005 | Akimoto et al. | 398/16 |
| 2005/0180748 A1* | 8/2005 | Kawahata | 398/16 |
| 2006/0008276 A1* | 1/2006 | Sakai et al. | 398/141 |
| 2007/0285582 A1* | 12/2007 | Hongo et al. | 348/723 |
| 2008/0200780 A1* | 8/2008 | Schenkman et al. | 600/310 |
| 2009/0058997 A1* | 3/2009 | Kato | 348/65 |
| 2009/0180743 A1* | 7/2009 | Althaus et al. | 385/101 |
| 2009/0234183 A1* | 9/2009 | Abe | 600/103 |

FOREIGN PATENT DOCUMENTS

| | | |
|---|---|---|
| JP | 2000-206422 A | 7/2000 |
| JP | 2006-026134 A | 2/2006 |
| JP | 2007-260066 A | 10/2007 |
| JP | 2007-301083 A | 11/2007 |
| JP | 2009-061032 A | 3/2009 |

* cited by examiner

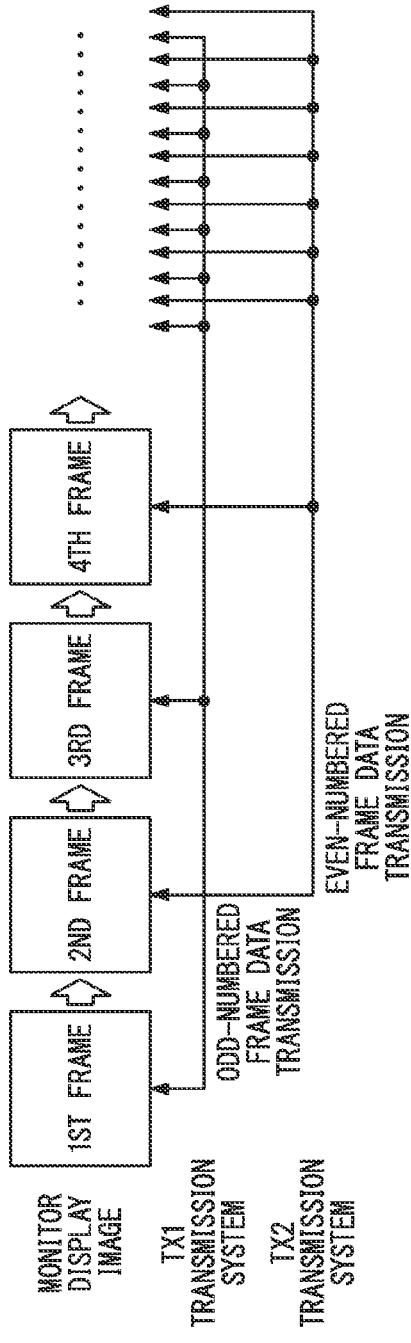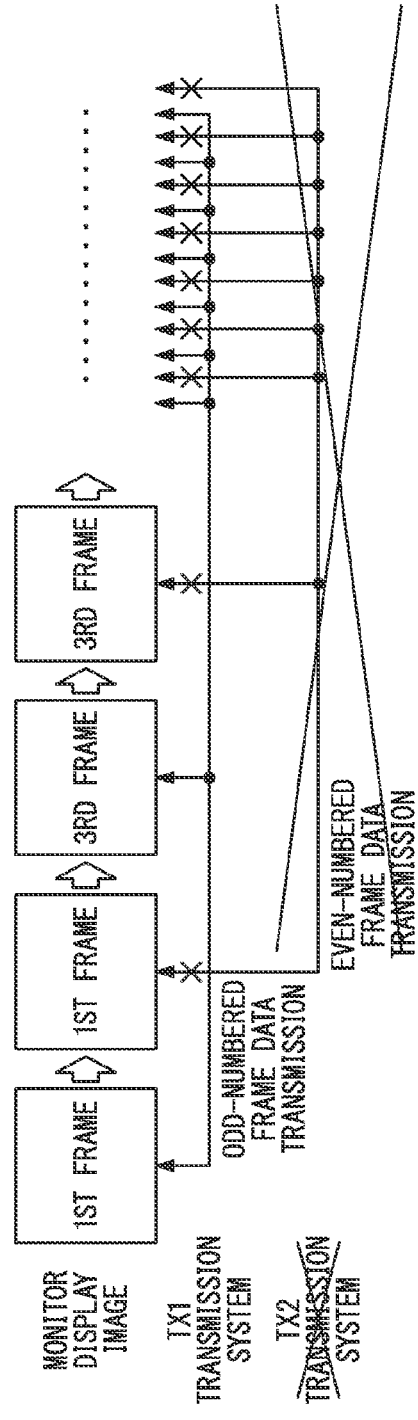

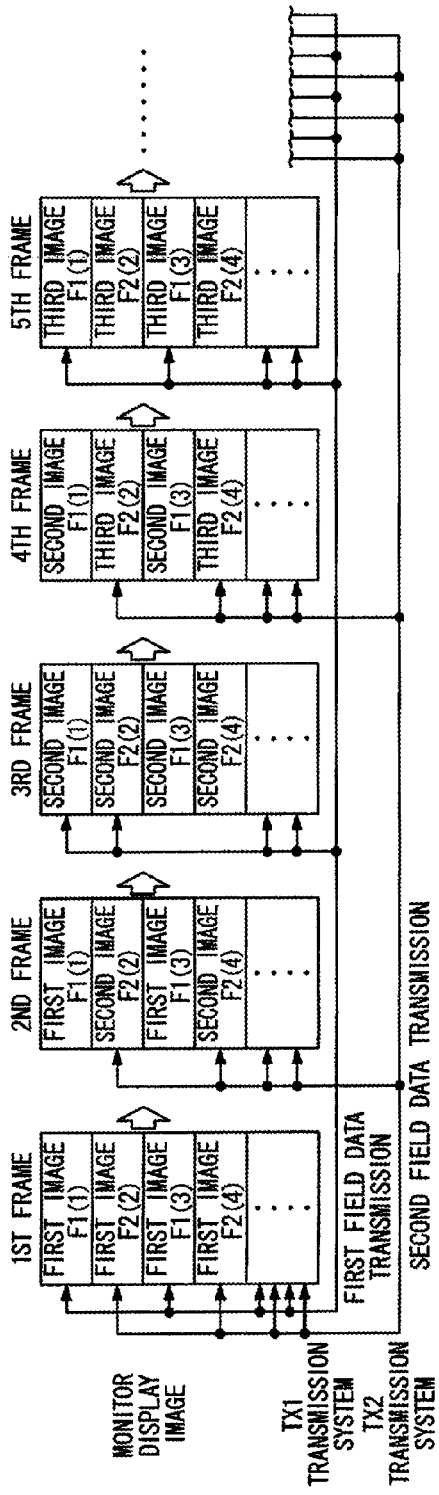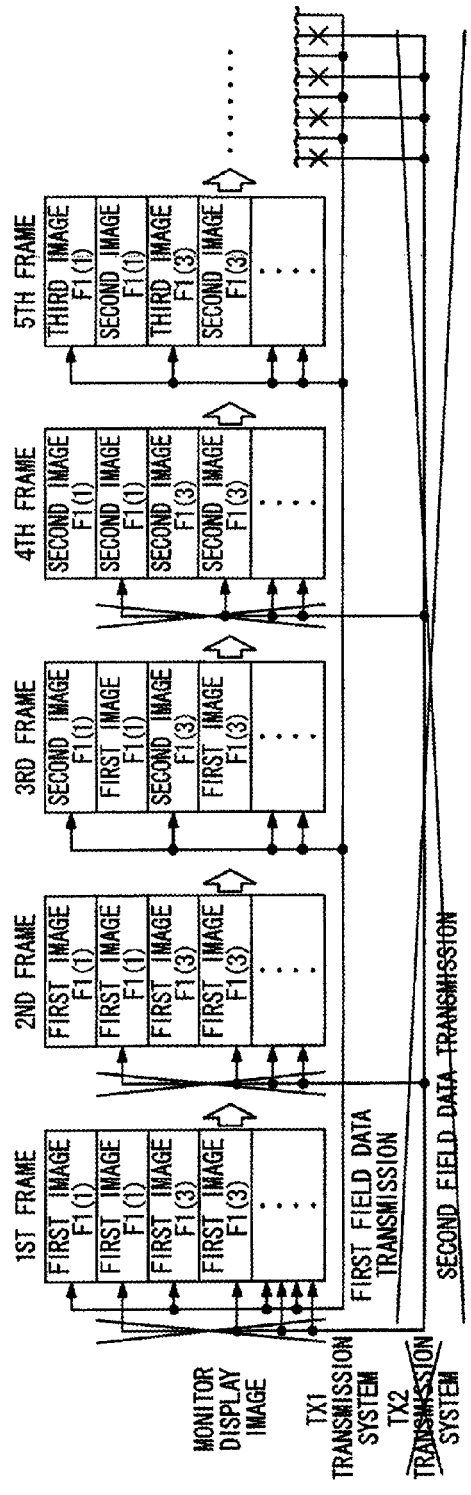

ENDOSCOPE SYSTEM

BACKGROUND OF THE INVENTION

1. Field of the Invention

The present invention relates to an endoscope system used by being inserted into a suspected substance, and more particularly to an endoscope system that transmits video signals via an optical fiber. Priority is claimed on Japanese Patent Application No. 2010-220157, filed on Sep. 30, 2010, the content of which is incorporated herein by reference.

2. Description of Related Art

Conventionally, typical endoscope systems utilizes a method in which video signals output from the image pickup device provided on a distal end portion of the endoscope to be inserted into a suspected substance are transmitted as analog signals to a video processor. Because typical endoscopes have a total length of several meters, the analog video signals are influenced by external noise during their transmission. As a result, the S/N ratio tends to be decreased, resulting in deteriorated image quality. In particular, in the medical front and the like that uses an endoscope system, a unit such as an electrosurgical knife is in operation. Therefore, noises at levels that are not present in a normal environment fly around, and their influences are extremely enormous.

To resolve this problem, Japanese Unexamined Patent Application, First Publication No. S61-121590 proposes an endoscope system utilizing a method in which video signals of the image pickup device are A/D-converted at the distal end portion of an endoscope and the digitized video signals are transmitted through the endoscope. If only High level and Low level of the signals are identified, video images will not be scrambled even if the digitized video signals are influenced by noise. Therefore, resistance to noise is improved.

In recent years, image pickup devices tend to be provided with higher resolution, resulting in an increase in the amount of data in signals. With this tendency, there is a demand for a higher transmission rate. In addition, there arises a need to set the amplitude of the digitized video signals small. As a result, even if video signals are digitized, conventional effects are less and less obtainable. Therefore, Japanese Unexamined Patent Application, First Publication, No. 2007-260066 proposes a technique of further converting the video signals, which have been A/D-converted at the distal end portion of the endoscope, to optical signals (performing E/O conversion), and then transmitting the video signals through an optical fiber.

SUMMARY OF THE INVENTION

According to a first aspect of the present invention, an endoscope system includes: an image pickup portion for picking up an image of a suspected substance and then producing a video signal; a plurality of optical fibers for transmitting the video signal output from the image pickup portion; a video signal processing portion for processing the video signals transmitted by the optical fibers and then outputting the processed video signals to an image display portion; and a trouble detection portion for detecting trouble in a transmission state of the optical fibers. In addition, the video signal processing portion outputs to the image display portion only the video signal transmitted by the optical fiber in which the trouble detection portion has not detected any trouble.

In the endoscope system according to the first aspect of the present invention, the optical fibers transmit the same video signal.

In the endoscope system according to the first aspect of the present invention, as for a plurality of frame images constituting a motion picture sequentially displayed on the image display portion, each of the optical fibers transmits the video signal constituting each frame image. In addition, all the video signals constituting the frame images are transmitted respectively by any of the optical fibers. Furthermore, if the trouble detection portion detects trouble in a transmission state of any of the optical fibers, the video signal processing portion outputs to the image display portion the video signal from the optical fiber with no detected trouble instead of the video signal from the optical fiber with the detected trouble.

In the endoscope system according to the first aspect of the present invention, as for a plurality of frame images constituting a motion picture sequentially displayed on the image display portion, each frame image is made of a plurality of regions, and each of the optical fibers transmits the video signal constituting each region. In addition, all the video signals constituting the regions in one of the frame images are transmitted respectively by any of the optical fibers. Furthermore, if the trouble detection portion detects trouble in a transmission state of any of the optical fibers, the video signal processing portion outputs the video signal from the optical fiber to the image display portion with no detected trouble instead of the video signal from the optical fiber with the detected trouble.

According to a second aspect of the present invention, the endoscope system further includes a test signal production portion for producing a plurality of test signals at different levels. In addition, the optical fibers transmit the test signals. Furthermore, the trouble detection portion measures an error rate of the test signals transmitted via the optical fiber as a target of trouble detection in order to check the transmission state, thereby detecting trouble in the transmission state.

The endoscope system according to the second aspect of the present invention further includes a test signal production portion for producing test signals with a certain level. In addition, the optical fibers transmit the test signals. Furthermore, the trouble detection portion receives, the test signals transmitted via the optical fiber with different sensitivities, as a target of trouble detection to measure an error rate, thereby detecting trouble in the transmission state.

In the endoscope system according to the second aspect of the present invention, the levels are modified in synchronicity with a cycle with which the optical fiber as a target of trouble detection transmits the video signals.

In the endoscope system according to the second aspect of the present invention, the reception sensitivities are modified in synchronicity with a cycle with which the optical fiber as a target of trouble detection transmits the video signals.

According to a third aspect of the present invention, the endoscope system further includes an alarm unit that notifies a user if the trouble detection portion detects a trouble in a transmission state of any of the optical fiber.

In the endoscope system according to the third aspect of the present invention, the optical fibers are spaced from each other by not less than 1 mm.

BRIEF DESCRIPTION OF THE DRAWINGS

FIG. 3 is a timing chart showing how frame data is transmitted in the embodiment of the present invention.

FIG. 4 is a timing chart showing how frame data is transmitted in the embodiment of the present invention.

DETAILED DESCRIPTION OF THE INVENTION

Figure 1:
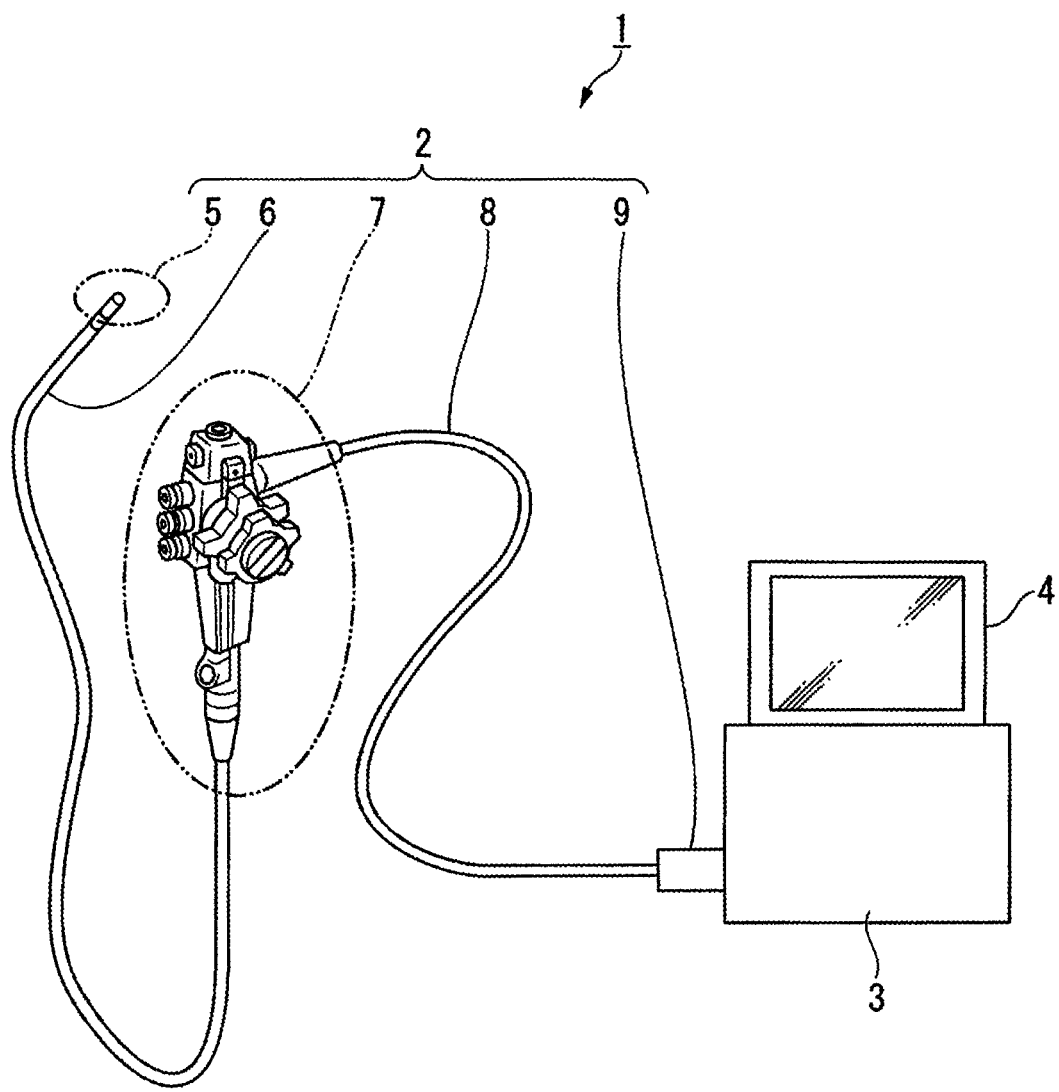
FIG. 1 is an external view showing an endoscope system according to an embodiment of the present invention.

Hereunder is a description of embodiments of the present invention with reference to the drawings. FIG. 1 shows a configuration of an endoscope system according to an embodiment of the present invention. As shown in FIG. 1, an endoscope system 1 includes: an endoscope 2 for obtaining video signals; a video processor 3 for processing the video signals obtained by the endoscope 2; and a monitor 4 for displaying the video signals, which have been processed as an image in the video processor 3. The endoscope 2 includes: a distal end portion 5 provided with an image pickup portion to be inserted into a suspected substance; an insertion portion 6 as a cord that guides the distal end portion 5 into the suspected substance; an operation portion 7 for operating the movement of the distal end portion 5 via the insertion portion 6; a universal cord 8, which is a cable that connects between the operation portion 7 and the video processor 3; and a connector portion 9, which is a detachable connector for connecting between the universal cord 8 and the video processor 3.

Figure 2:
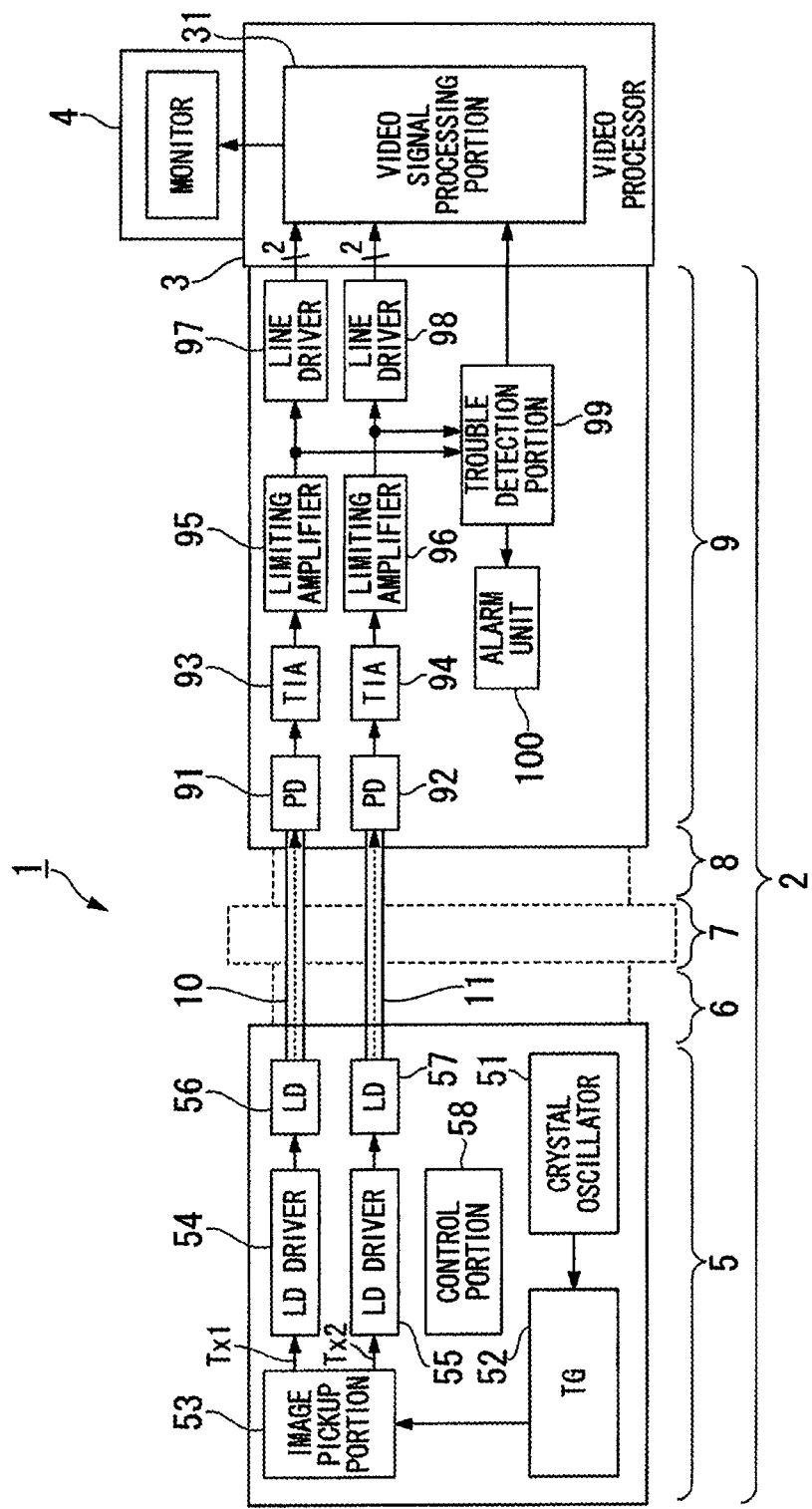
FIG. 2 is a block diagram showing a functional configuration of the endoscope system according to the embodiment of the present invention.

FIG. 2 specifically shows an internal function of the skeleton framework configuration shown in FIG. 1.

The distal end portion 5 includes: a crystal oscillator 51; a TG 52; an image pickup portion 53; LD drivers 54 and 55; LDs 56 and 57; and a control portion 58. The crystal oscillator 51 produces highly accurate clock functioning as a source of drive pulses (such as horizontal synchronization signals and vertical synchronization signals) necessary for driving the image pickup portion 53. The TG 52 produces drive pulses for the image pickup portion 53 based on the clock output from the crystal oscillator 51. The image pickup portion 53 picks up an image of the suspected substance to produce video signals, and outputs the video signals via a channel Tx1 and a channel Tx2.

The LD drivers 54 and 55 produce signals for driving laser diodes (LDs). Based on the drive signals from the LD drivers 54 and 55, the LDs 56 and 57 respectively convert the video signals of the channels Tx1 and Tx2 to optical signals, and transmit them to optical fibers 10 and 11. The control portion 58 controls the aforementioned respective constituent elements. In FIG. 2, illustrations of control signals output from the control portion 58 to the respective constituent elements are omitted.

The optical fibers 10 and 11 transmit the video signals in the channels Tx1 and Tx2, which have been produced in the distal end portion 5, to the connector portion 9 as optical signals.

The connector portion 9 includes: PDs 91 and 92; TIAs 93 and 94; limiting amplifiers 95 and 96; line drivers 97 and 98; a trouble detection portion 99; and an alarm unit 100. The PDs 91 and 92 convert the optical signals in the channels Tx1 and Tx2, which have been transmitted via the optical fibers 10 and 11, to electric currents. The TIAs 93 and 94 convert the electric currents sent from the PDs 91 and 92 to voltages. The limiting amplifiers 95 and 96 amplify and binarize minim signals transmitted from the TIAs 93 and 94.

The line drivers 97 and 98 convert the binarized signals from the limiting amplifiers 95 and 96 to differential signals, and differentially transmit them to the video processor 3. The trouble detection portion 99 receives the signals transmitted from the limiting amplifiers 95 and 96 to detect trouble in the transmission state of the optical fibers 10 and 11. A specific detection method of troubles in the transmission state will be described later. On receiving the information of "trouble detected" from the trouble detection portion 99, the alarm unit 100 sounds an alarm buzzer.

The video processor 3 includes a video signal processing portion 31 that, based on the trouble detection signal from the trouble detection portion 99, processes the video signals from the line drivers 97 and 98 and outputs a video image to the monitor 4. If the trouble detection portion 99 detects trouble in the transmission state of either of the optical fibers 10 and 11, the video signal processing portion 31 outputs only the video signals, which have been transmitted via the optical fiber with no detected trouble, to the monitor 4. The details of this will be described later.

Next, with reference to FIGS. 3A, 3B and FIGS. 4A, 4B, the operation of the endoscope system 1 will be described in further detail. A video image displayed by the monitor 4 is a frame image made of a plurality of frames (a 1st frame, a 2nd frame, a 3rd frame, . . . ). The video signals constituting each frame image (hereinafter, referred to as frame data) are transmitted from the distal end portion 5 to the connector portion 9 as described below.

FIG. 3A and FIG. 3B show a first example of a transmission. In the endoscope system 1, as shown in FIG. 3A, pieces of frame data are transmitted in a transmission system for each of the channels Tx1 and Tx2. To be more specific, the pieces of data on the odd-numbered frames are transmitted via the transmission system for the channel Tx1, and the even-numbered frames are transmitted via the transmission system for the channel Tx2. Thus, each piece of frame data constituting each frame image is transmitted by the transmission system for either channel Tx1 or Tx2.

While receiving signals of "no trouble detected" from the trouble detection portion 99, the video signal processing portion 31 causes the monitor 4 to alternately display a piece of data of an odd-numbered frame and a piece of data of an even-numbered frame as a monitor display image, as shown in FIG. 3A. However, on receiving the information of "trouble detected" from the trouble detection portion 99, the video signal processing portion 31 causes the monitor 4 to display the pieces of data for the transmission system with no detected trouble instead of the pieces of data for the transmission system with detected trouble, as shown in FIG. 3B.

FIG. 3B shows a case of an occurrence of trouble in the transmission system for the channel Tx2. As shown in FIG. 3B, the video signal processing portion 31 causes the monitor 4 to display the pieces of odd-numbered frame data consecutively, instead of the pieces of even-numbered frame data. To be more specific, instead of the piece of data of the 2nd frame, the piece of data of the 1st frame, which is the one directly prior to the 2nd frame, is displayed on the monitor 4. In addition, instead of the piece of data of the 4th frame, the piece of data of the 3rd frame, which is the one directly prior to the 4th frame, is displayed on the monitor 4.

FIG. 4 shows a second example of a transmission. In this case, each frame data is made of: data in a first field corresponding to odd-numbered scan lines; and data in a second field corresponding to even-numbered scan lines. As shown in FIG. 4A, the endoscope system 1 transmits data of each field through the transmission system for each of the channels Tx1 and Tx2. To be more specific, the data in the first field is transmitted through the transmission system for the channel Tx1, and the data in the second field is transmitted through the transmission system for the channel Tx2. In this manner, the pieces of data in the fields constituting the frame data are transmitted through a transmission system for either of the channels Tx1 and Tx2.

While receiving signals of "no trouble detected" from the trouble detection portion 99, the video signal processing portion 31 forms data of frames by combining the data in the first field and the data in the second field in an alternate manner as shown in FIG. 4A, and cause the monitor 4 to display the resultant data. In FIG. 4A, "F1" designates the first field, and "F2" designates the second field. In addition, a numeral in parentheses designates the order of a scan line. Furthermore, "first" of a "first image" designates a temporal order of an image picked up in the image pickup portion 53. For example, a first image F1(1) indicates an image data obtained first in the temporal order at the position of the first scan line of the first field in the image pickup portion 53.

For the first frame to be displayed, the video signal processing portion 31 causes the monitor 4 to display frame data in which odd-numbered scan lines are made of the data in the first field of the first image and even-numbered scan lines are made of the data in the second field of the first image. Subsequently, for the second frame to be displayed, the video signal processing portion 31 produces frame data by substituting the pieces of the data of the second field of the first image, which were displayed directly therebefore, with the pieces of the data of the second field of second image, and causes the monitor 4 to display the produced frame data.

Subsequently, for the third frame to be displayed, the video signal processing portion 31 produces frame data by substituting the pieces of the data of the first field of the first image, which were displayed directly before, with the pieces of the data of the first field of the second image, and causes the monitor 4 to display the produced frame data. Subsequently, for the fourth frame to be displayed, the video signal processing portion 31 produces frame data by substituting the pieces of the data of the second field of the second image, which were displayed directly before, with the pieces of the data of the second field of the third image, and causes the monitor 4 to display the produced frame data. Hereafter, the video signal processing portion 31 continues the similar operation.

On receiving a "trouble detected" signal from the trouble detection portion 99, the video signal processing portion 31 causes the monitor 4 to display the data for the transmission system with no detected trouble instead of the data for the transmission system with a detected trouble, as shown in FIG. 4B. FIG. 4B shows an example of case of an occurrence of a trouble in the transmission system for the channel Tx2. As shown in FIG. 4B, the video signal processing portion 31 uses the data of the first field, instead of the data of the second field, to form data of a frame only by the data of the first field.

If there is trouble in the transmission system for the channel Tx2, the pieces of data of the first field is displayed by the video signal processing portion 31 again one line below in the lines of the 1st frame and the even-numbered frames of FIG. 4B in which the pieces of data of the second field are displayed. The timing of this processing is the same as that when the pieces of the data of the second field in the case with no trouble are to be displayed in the 1st frame and the even-numbered frames in FIG. 4A.

To be more specific, for the first frame, the second frame, and the fourth frame to be displayed, the video signal processing portion 31 causes the pieces of data of the first field that are the same as those in the odd-numbered lines from the top to be displayed also in the even-numbered lines below the odd-numbered lines, which are the lines in which the pieces of data in the second field are to be originally displayed. Hereafter, the video signal processing portion 31 continues the similar operation.

Thus, according to the endoscope system of the present embodiment, it is possible to check the state of transmission of the optical fibers while an image is being displayed on the monitor 4. If trouble is detected, it is possible to continue the display of the image by use of the pieces of data in the frame or fields of the transmission with no trouble instead of the pieces of data in the frame or fields of the transmission with the detected trouble. Therefore, even if there is trouble in some part of the transmission in the optical fibers, display of the video is not interrupted, and hence, the risk of abrupt interruption of the video when the endoscope is in use due to the problem of the transmission systems is decrease. Furthermore, the same video data is not redundantly transmitted through a plurality of optical fibers. This prevents the electric power consumed in signal transmission from increasing excessively, thus suppressing the influence on heating.

In the present embodiment, a plurality of optical fibers transmit different video data, and the data is not redundantly transmitted. However, in another embodiment of the present invention, a plurality of optical fibers may redundantly transmit the same video signal. In this case, with the same data being transmitted redundantly, the transmission rate increases, and the electric power consumed in data transmission increases. In addition, a multitude of expensive parts capable of transmitting signals at high speeds are required, which increases costs. However, even if there is trouble in the transmission in some part of the optical fibers, an effect can be obtained in that the display of the images before and after the trouble are not influenced at all.

Next, with reference to the flow chart of FIG. 5, a flow of trouble detection according to the present embodiment will be described.

Here, the endoscope system 1 according to the present invention is capable of sending test data from the image pickup portion 53 with the luminescence intensity of the LDs 56 and 57 being set to 10 stages (output level 1 to output level 10). In addition, in the endoscope system 1 according to the present embodiment, a bit error rate of the test data can be measured in the trouble detection portion 99. Furthermore, as criteria for trouble in the endoscope system 1 of the present invention, the transmission state is determined as favorable (with no trouble) if the output level is not more than level 5 and is also error free (without an error), and the transmission state is determined as unfavorable (with trouble) if the output level is level 5 and also has an error (with an error).

Figure 5:
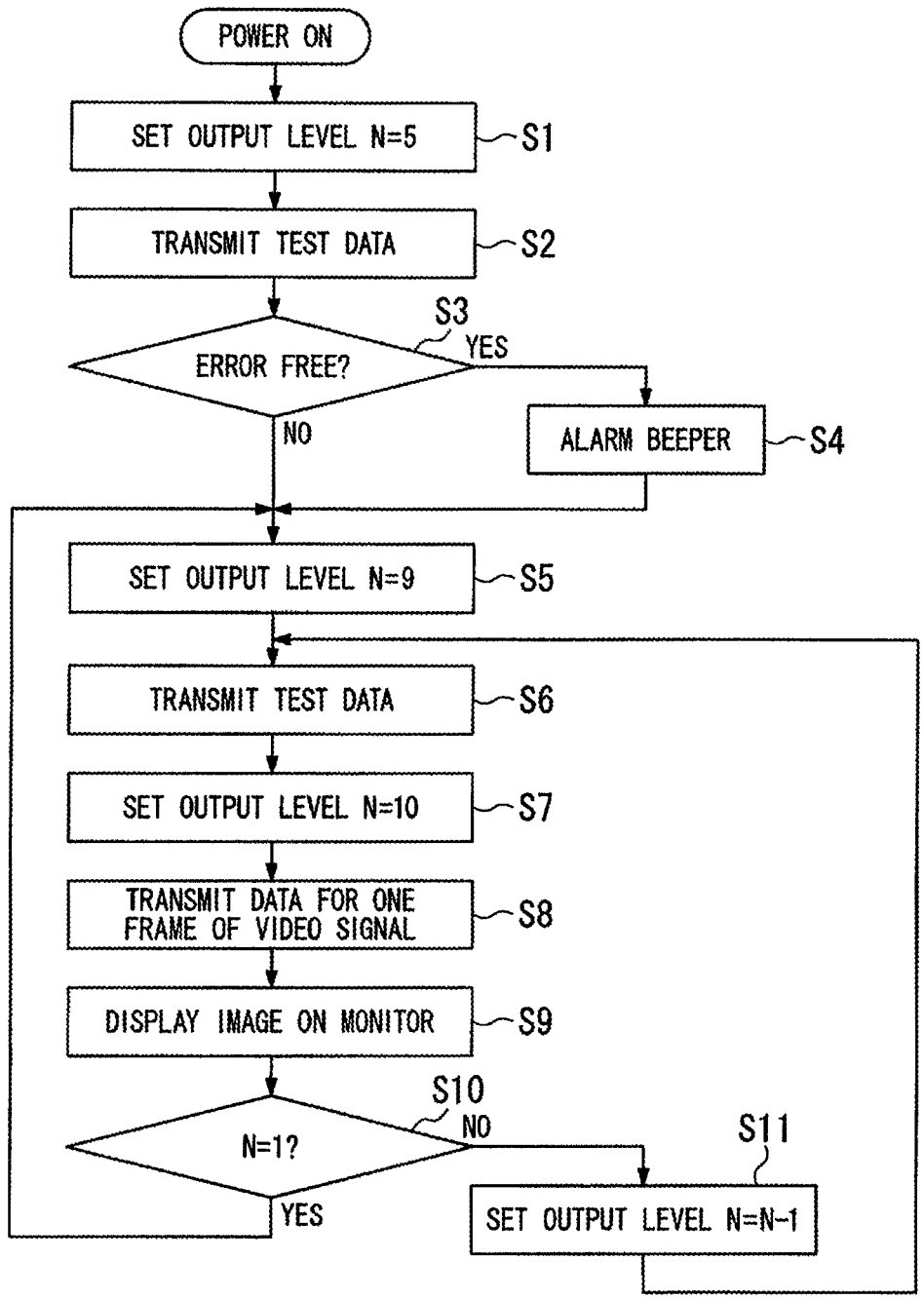
FIG. 5 is a flow chart showing a flow of processes involved in trouble detection in the embodiment of the present invention.

Hereunder is a description of the steps in the flow chart of FIG. 5. When the endoscope system 1 is turned ON, the endoscope system 1 detects the transmission state directly after the power is turned on. If the transmission state is faulty, an alarm beeper is sounded (steps S1 to S4). Below, the details of steps S1 to S4 will be described in this order.

First, the control portion 58 sets the levels of luminescence intensity (hereinafter, each referred to as output level) of the LDs 56 and 57 to level 5 (step S1). Subsequently, the image pickup portion 53 produces test data, and the test data is transmitted to the connector portion 9 via the channels Tx1 and Tx2 (step S2). The trouble detection portion 99 calculates a bit error rate based on the received test data to determine whether an error has occurred or not (step S3).

If an error has not occurred (error free), the process proceeds to step S5. If an error has occurred, the trouble detection portion 99 outputs the information of "trouble detected" to the alarm unit 100, and sounds an alarm beeper (step S4). After that, the process proceeds to step S5.

Subsequently, the endoscope system 1 transmits the video signals produced by the image pickup portion 53 to the video processor 3 and displays a video image on the monitor 4. In the present embodiment, the endoscope system 1 transmits test data at a different output level for detecting the transmission state every time the data for one frame of video signals is transmitted, and displays a video image (steps S5 to S11), while checking the transmission state. The details of this will be described in this order below.

Firstly, the control portion 58 sets the output level to level 9 for transmission of text data (step S5). Subsequently, the image pickup portion 53 produces test data, and the test data is transmitted to the connector portion 9 via the channels Tx1 and Tx2 (step S6). Subsequently, the control portion 58 sets the output level to level 10 for transmission of video signals (step S7). Subsequently, the image pickup portion 53 produces video signals for one frame, and the video signals are transmitted to the connector portion 9 via the channels Tx1 and Tx2 (step S8). The video signal processing portion 31 performs the aforementioned processing to output video signals to the monitor 4, and causes an image to be displayed (step S9).

Subsequently, the control portion 58 determines the output level for transmission of the current test data (step S10). If the output level for transmission of the current test data is 1, the process returns to step S5. If the output level for transmission of the current test data is not 1, the control portion 58 sets the output level for transmission of test data to the level lower than the current output level by 1 (step S11). Subsequently, the process returns to step S6. Through steps S5 to S11, the output level for test data is decreased from level 9 to level 1 in 1 level steps. When the output level of the test data is decreased to 1, the output level is set to 9 again, and the test data is repeatedly transmitted. During that time, video signals are transmitted at output level 10 frame by frame.

In parallel with the processes in steps S5 to S11, the trouble detection portion 99 performs the following processes. Based on the received test data, the trouble detection portion 99 calculates a bit error rate to determine whether an error has occurred or not. Because the output level of the test data decreases from level 9 to level 1 in 1 level steps, the trouble detection portion 99 detects an occurrence of an error when the error free switches to the error. The output level when the error free switches to the error can be determined to be a border level between the error and the error free. In the present embodiment, the border level at which the error free has switched to the error is defined as a transmission level. The smaller the numerical value of the transmission level is, the more favorable the transmission state is. The transmission level is displayed on the monitor 4.

If an error has occurred, the trouble detection portion 99 further determines whether or not the transmission level is not less than 5. If the transmission level is not less than 5, the trouble detection portion 99 determines that the transmission state is faulty, and outputs the information of "trouble detected" to the alarm unit 100 to sound the alarm beeper. Hereafter, based on the trouble detection signal from the trouble detection portion 99, the video signal processing portion 31 uses only the video signals transmitted via the transmission system for a channel with no error to cause the monitor 4 to display an image.

In the present embodiment, the transmission level is checked by modifying the levels of luminescence intensity of the LDs 56 and 57. However, the transmission level may be similarly checked by modifying the levels of reception sensitivity of the PDs 91 and 92. For example, if the levels of reception sensitivity of the PDs 91 and 92 can be set to 10 stages (output level 1 to output level 10) and test data with a specified luminescence intensity can be transmitted from the image pickup portion 53, then it is possible to obtain transmission levels in a flow similar to that of the flow chart of FIG. 5 (in which output levels in steps S1, S5, S7 and S11 are substituted with the levels of reception sensitivity).

Thus, an error rate is measured while modifying the luminescence levels or levels of reception sensitivity, to thereby make it possible to grasp the specific transmission level in addition to the presence or absence of a trouble. Therefore, the user can prepare for fixing and maintenance at more precise timing. For example, it is possible to maintain an endoscope system, whose transmission state is not so good although it is not at the level of trouble, before an important surgery.

Furthermore, in the trouble detection processing according to the present embodiment, a measurement of test data at one level is performed in a between-frame period (a period between a frame transmission and a frame transmission). Namely, in the trouble detection processing according to the present embodiment, by adopting a flow that measures test data at different levels in synchronicity with the cycle for transmitting video signals, it is possible to measure test data at a plurality of levels in a distributed time. As a result, the measurement time for test data spent in a between-frame period can be made short, and the transmission level can be detected even performing image at a high frame rate. For example, if the test data at all levels is to be measured in a between-frame period in order to obtain a transmission level for every frame, the measurement of the test data for one level requires a span of 1 ms. If the measurement of nine pieces of test data are required for detection of a transmission level, then a span of 9 ms is required to detect the transmission level. Here, in the trouble detection processing according to the present embodiment, if test data for one level is measured in every between-frame period, then measurement of test data for nine levels over 10 frames can lead to detection of a transmission level. Therefore, the measurement time for the test data in the between-frame periods is only 1 ms. For example, in the case of a frame rate of 120 fps, the between-frame period is only 8.3 ms. As a result, it is not possible to spend 9 ms in a row for detection of a transmission level.

Furthermore, in the present embodiment, when trouble in the transmission state is detected, the user is notified of the trouble in the transmission state with an alarm beeper. This operation has an effect of prompting the user to be ready for repair. In the present embodiment, a beeper is used for notifying the user of trouble. However, the device to warn to the user (the warning device of the alarm unit) is not limited to this. A warning may be displayed on the monitor, or other methods may be adopted.

Figure 6:
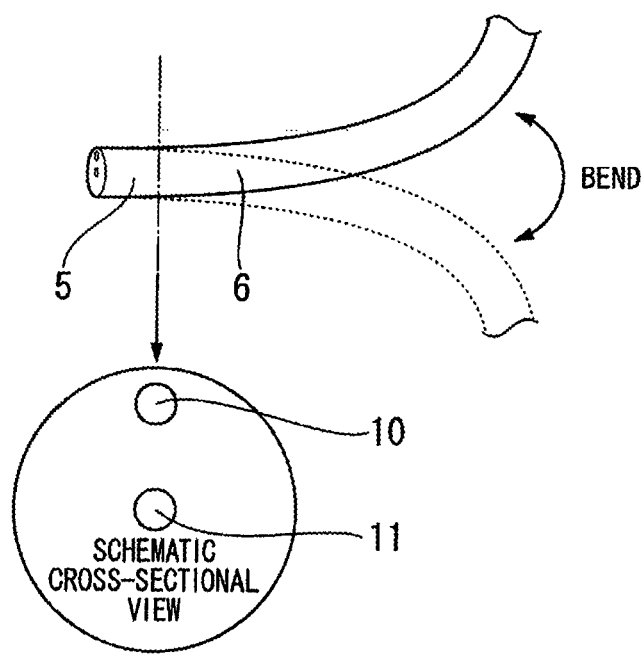
FIG. 6 is a pattern diagram showing a cross-section of a connection portion between a distal end portion and an insertions portion of the endoscope system according to the embodiment of the present invention.

FIG. 6 shows a cross-section of a connection portion between the distal end portion 5 and the insertion portion 6 in the endoscope system 1 according to the present embodiment. As shown in FIG. 6, in the distal end portion 5, the optical fiber 10 and the optical fiber 11 are spaced from each other so that the optical fiber 10 is located on an outer side of the insertion portion 6 and the optical fiber 11 is located at the central portion of the insertion portion 6. It is desirable that the distance between the two optical fibers be not less than 1 mm.

As described above, transmission of video signals by use of a plurality of optical fibers makes it possible to reduce the risk of abrupt interruption of a video image due to the problem of the transmission system when the endoscope is used. However, if all the optical fibers rupture at the same time, it is not possible to obtain the advantageous effect. As shown in FIG. 6, by the optical fibers used for transmission of video signals being arranged in a spaced manner, mechanical loads acting on the optical fibers are different every optical fibers when the insertion portion 6 is bent.

Therefore, it is possible to reduce the risk of simultaneous rupture of all the optical fibers. Consequently, it is possible to further reduce the risk of abrupt interruption of a video image due to the problem of the transmission system when the endoscope is used.

In the present embodiment, video signals are divided into odd-numbered frames and even-numbered frames and transmitted via two optical fibers as shown in FIG. 3. However, the number of optical fibers is not limited to two. Depending on the situation, the frame may be further divided to increase the number of optical fibers for transmission. Furthermore, as shown in FIG. 4, the video signals are transmitted by being divided into the field for odd-numbered scan lines and the field for even-numbered scan lines. However, the configuration for transmission is not limited to one in which the region is divided for every field. For example, the region may be divided by other methods such as dividing the region by lines in the vertical direction. If a CMOS sensor is used for the image pickup portion, it is possible to define the read region of the video signals comparatively freely. Therefore, even in the case where the region is complicatedly divided when the signals are transmitted, it is possible to coincide the read regions of the video signals with the complicatedly divided region, thus simplifying the signal processing.

As described above, according to the present embodiment, the video signals output from the image pickup portion are transmitted via a plurality of optical fibers, and only the video signals that have been transmitted via the optical fibers with no detected trouble are used for display. Thereby, even if trouble occurs in an optical fiber, it is possible to reduce the risk of abrupt interruption of a video image.

While embodiments of the present invention have bee described in detail with reference to the drawings, the specific configuration is not limited to those of the embodiments, and design modification without departing from the sprit or scope of the present invention is included.

What is claimed is:

1. An endoscope system, comprising:
    an image pickup portion for picking up an image of a suspected substance and then producing a first video signal;
    a plurality of optical fibers for transmitting the first video signal output from the image pickup portion;
    a video signal processing portion for processing the first video signals transmitted by the optical fibers and then outputting the processed first video signals to an image display portion; and
    a trouble detection portion for detecting trouble in a transmission state of the optical fibers,
    wherein the processed first video signal includes a plurality of first frame images and a plurality of second frame images,
    wherein each of the plurality of first frame images and the plurality of second frame images are transmitted along corresponding one of the optical fibers, and
    wherein, if the trouble detection portion detects trouble in the optical fibers transmitting the first frame images, the video signal processing portion outputs the second frame images to the image display portion, and a second video signal is made by the second frame images in the image display portion.

2. The endoscope system according to claim 1, wherein the optical fibers transmit the same first video signal.

3. The endoscope system according to claim 1, further comprising
    a test signal production portion for producing a plurality of test signals at different levels,
    wherein the optical fibers transmit the test signals, and
    wherein the trouble detection portion measures an error rate of the test signals transmitted via the optical fiber, as a target of trouble detection, to check a transmission state, thereby detecting trouble in the transmission state.

4. The endoscope system according to claim 3,
    wherein the levels are modified in synchronicity with a cycle with which the optical fiber as a target of trouble detection transmits the first video signals.

5. The endoscope system according to claim 1, further comprising
    a test signal production portion for producing test signals at a constant level,
    wherein the optical fibers transmit the test signals, and
    wherein the trouble detection portion receives, with different reception sensitivities, the test signals transmitted via the optical fiber, as a target of trouble detection, to measure an error rate, thereby detecting trouble in the transmission state.

6. The endoscope system according to claim 5,
    wherein the reception sensitivities are modified in synchronicity with a cycle with which the optical fiber as a target of trouble detection transmits the first video signals.

7. The endoscope system according to claim 1, further comprising
    an alarm unit that notifies a user if the trouble detection portion detects trouble in a transmission state of any of the optical fiber.

8. The endoscope system according to claim 1,
    wherein the optical fibers are spaced from each other by not less than 1 mm.

* * * * *